United States Patent [19]
Vadas

[11] 3,943,916
[45] Mar. 16, 1976

[54] SURGICAL INSTRUMENT FOR CONIZATION OF THE CERVIX

[76] Inventor: Leslie Vadas, 135 Riviera Drive, Los Gatos, Calif. 95030

[22] Filed: Dec. 26, 1974

[21] Appl. No.: 536,345

Related U.S. Application Data

[63] Continuation of Ser. No. 424,410, Dec. 13, 1973, abandoned.

[52] U.S. Cl. ................................. 128/2 B; 128/305
[51] Int. Cl.² .......................................... A61B 10/00
[58] Field of Search ........ 128/304, 305, 305.1, 314, 128/311, 3, 2 B; 408/157, 158, 159, 161; 30/300, 310; 82/1.2, 1.4

[56] References Cited
UNITED STATES PATENTS

| | | | |
|---|---|---|---|
| 3,147,749 | 9/1964 | Marsh | 128/305 |
| 3,357,422 | 12/1967 | Creelman | 128/305 |
| 3,628,522 | 12/1971 | Kato | 128/305 |
| 3,702,611 | 11/1972 | Fishbein | 128/305 |

*Primary Examiner*—John D. Yasko
*Attorney, Agent, or Firm*—C. E. Tripp

[57] ABSTRACT

An instrument for cold conization of the cervix includes a pair of round nose, pivoted blades which are advanced by a camming mechanism as the instrument is rotated. During rotation of the blades they are progressively cammed to their closed position by a sliding actuator, thereby providing a continuous helicoid cut. The blade operating mechanism does not protrude beyond the diameter of the blades themselves at any time. In one form of the invention a screw mechanism causes automatic advance of the blades to produce a helicoid cut upon rotation of the body by the actuator.

9 Claims, 17 Drawing Figures

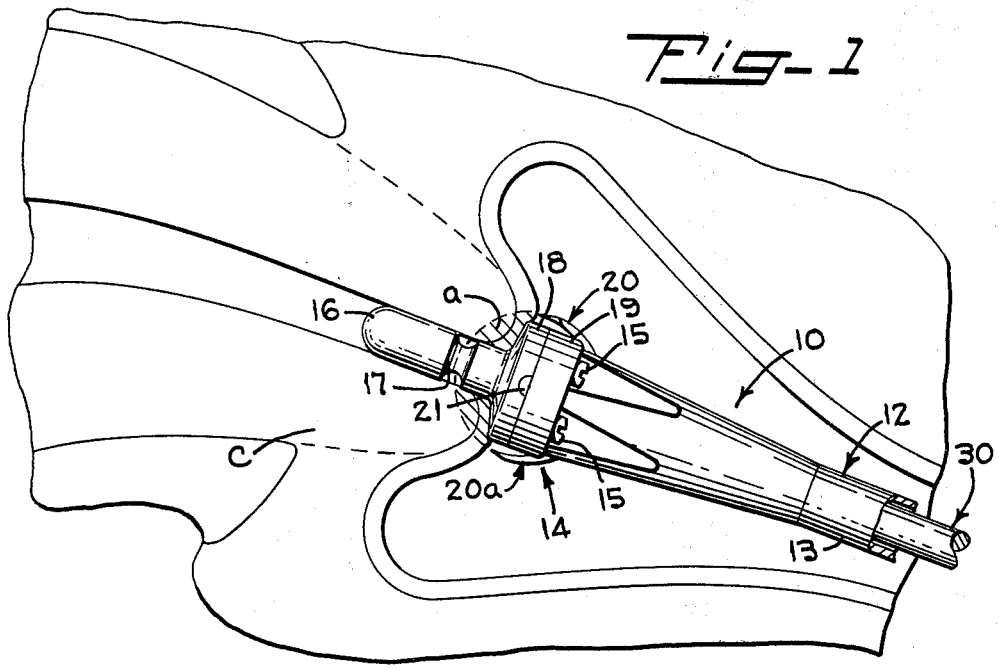
Fig-1
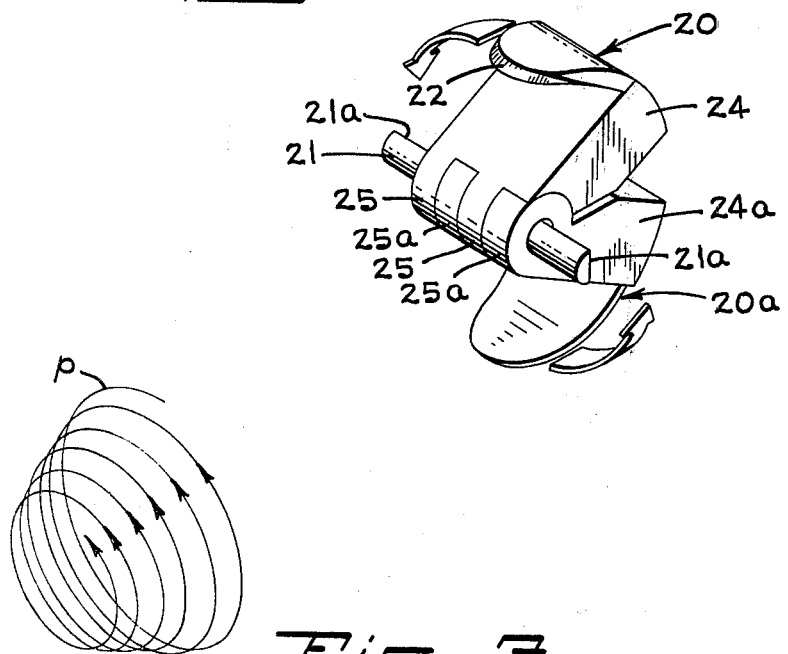
Fig-2
Fig-3

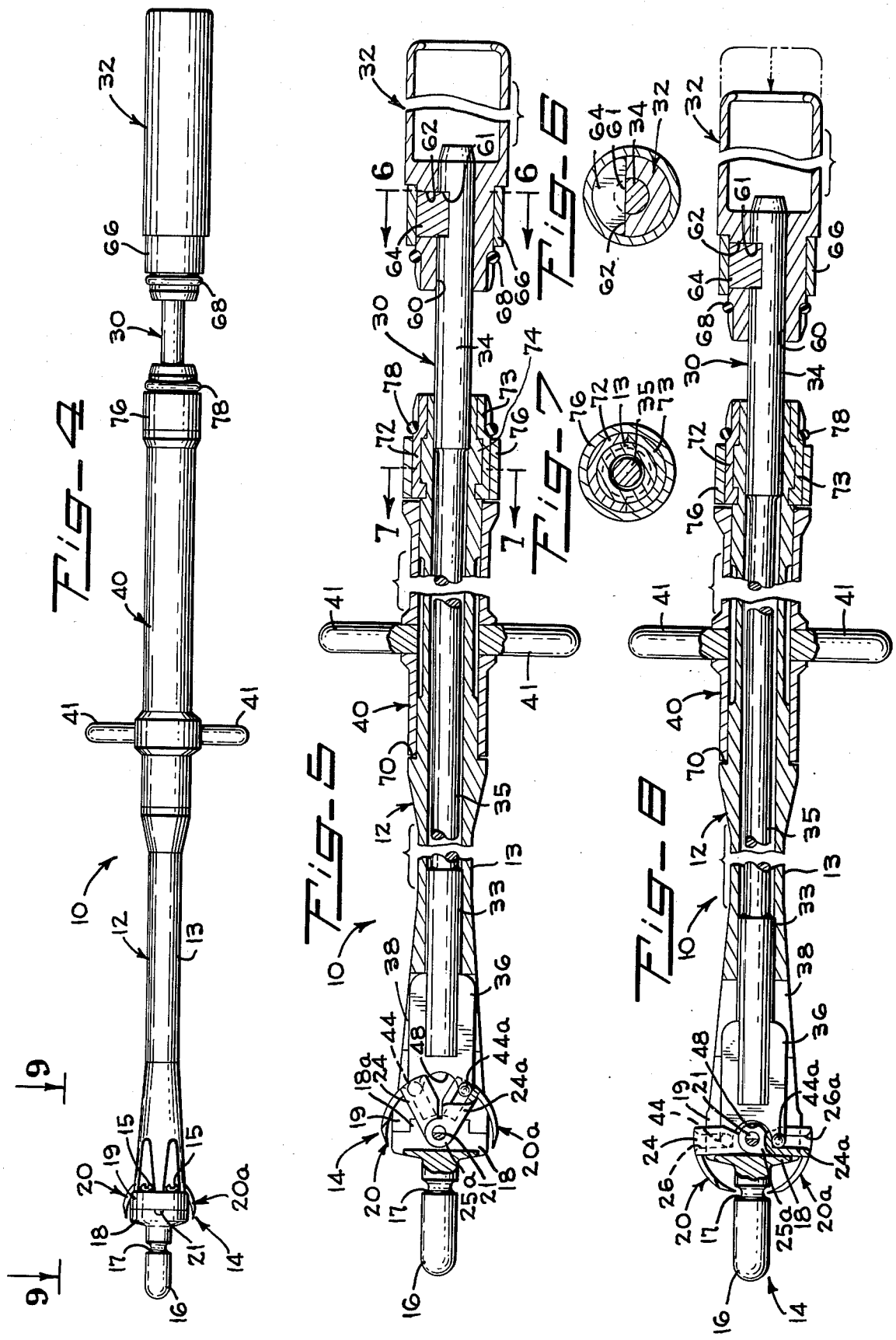

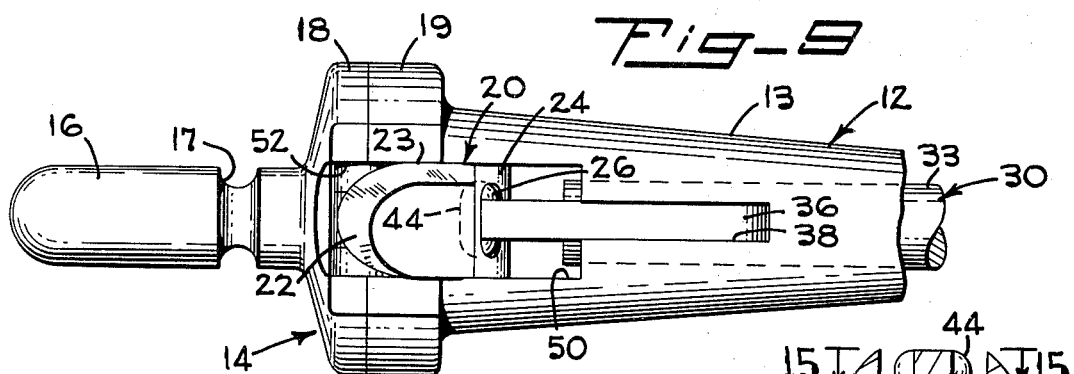
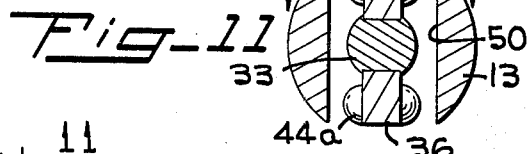
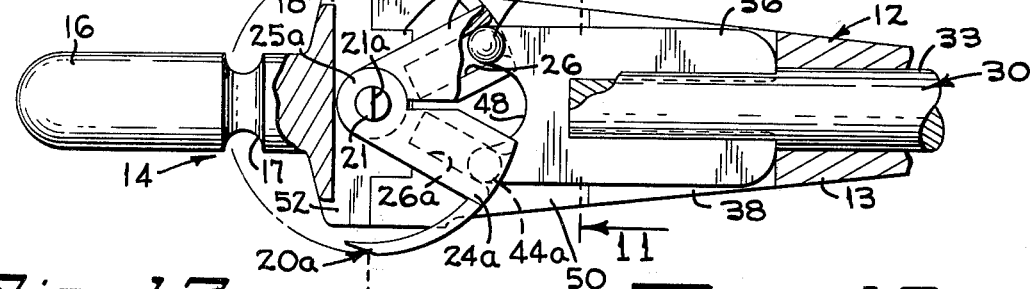
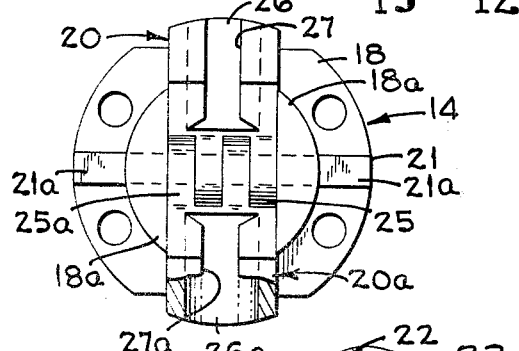
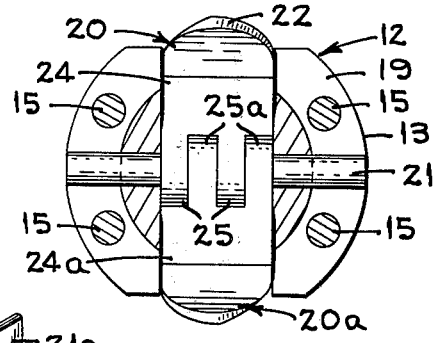
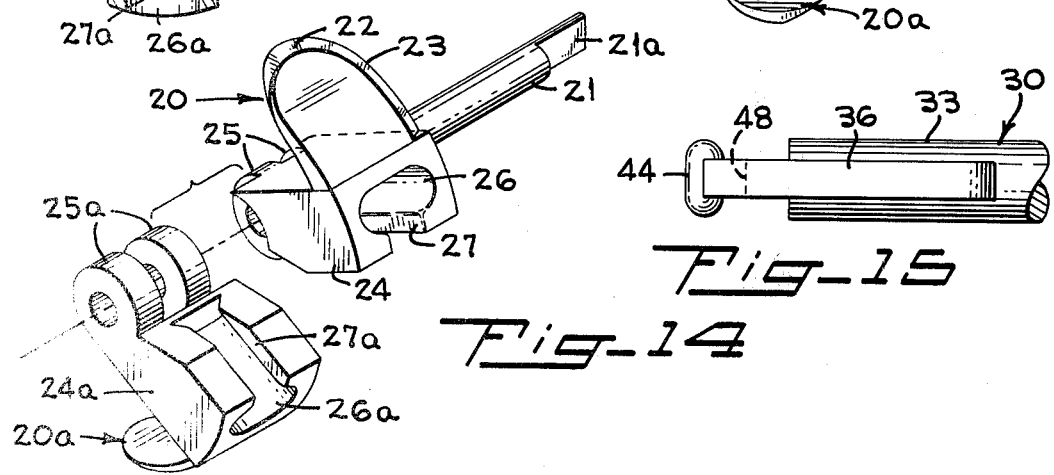

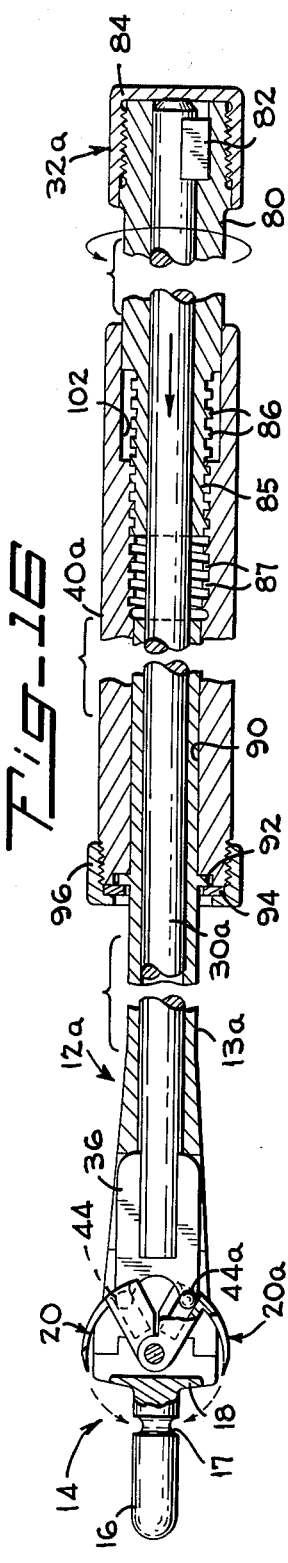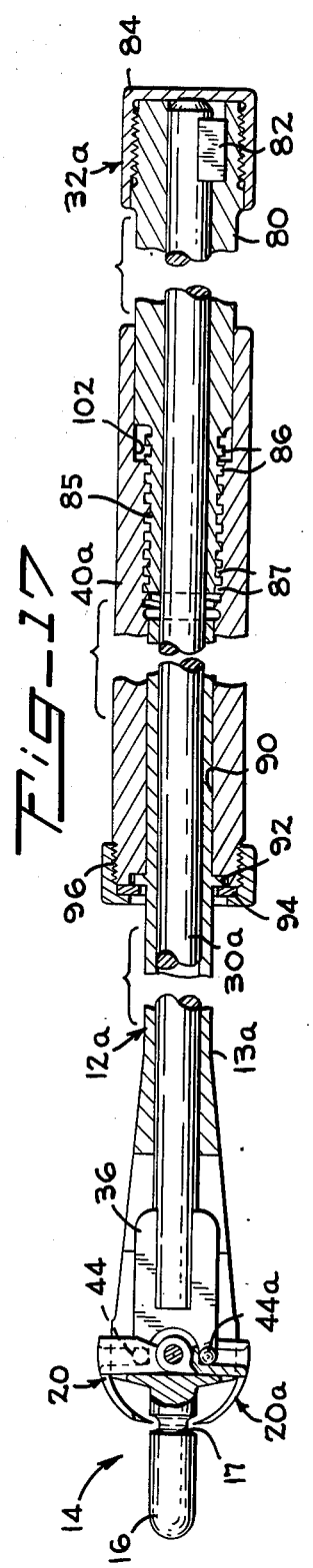

SURGICAL INSTRUMENT FOR CONIZATION OF THE CERVIX

This is a continuation of application Ser. No. 424,410, filed Dec. 13, 1973, now abandoned.

DESCRIPTION OF PRIOR ART

The U.S. Pat. to Marsh, No. 3,147,749, Sept. 8, 1964 discloses a cold conization instrument using non-rotary semi-spherical blades that are simply closed to produce a cutting action.

The U.S. Pat. to Kato, No. 3,628,522, Dec. 21, 1971 describes a conization instrument wherein two blades are pivotally mounted in a body and are advanced by a pair of sliding rods actuated by a screw mechanism when the body and rods are rotated. Due to the linkage arrangement between the rods and the blades, the blades, their mountings and their operating rods provide protuberances and since these elements are rotated during the operation, these protuberances will rotate with the instrument body.

The U.S. Pat. to Creelman, No. 3,357,422, Dec. 12, 1967 shows an instrument for conization of the cervix having a single blade that is pivoted on one side of the body and disposed on the opposite side thereof, and is operated by a sliding rod and linkage mechanism. This device is operated by first sequentially forming a sequence of plunging cuts and by then severing the specimen between the cuts by a one revolution operation of the instrument. Due to the manner in which the single blade is pivotally mounted on the body, protuberances are provided that will rotate with the instrument body upon rotation of the body during the operation.

SUMMARY OF THE INVENTION

The instrument of the present invention is designed to perform the operation in question by a process which will be termed "helicoid cutting". The instrument has a pair of round nosed blades that lie within a semi-spherical element. The principal elements of the instrument in one embodiment include a relatively small diameter rotatable body that pivotally mounts opposed pair of round nosed, side cutting blades. The blades are retained in the body by a removable body end that includes a tip or obturator for insertion into the cervical canal. Assembly of the tip and body retains the blades by simply gripping the ends of a pivot pin for the blades, which pin also extends through the tip member. The blades are advanced and retracted by a cam mechanism that lies totally within the confines of the generally smooth cylindrical body. This mechanism includes an actuator rod slidable in the body and having a pair of integral cams that slide in cam grooves formed in pivoted arms that mount the blades. The construction is such that there are no obstructions at the operating zone to damage surrounding tissue during rotation of the body for performance of the operation. A grip is loosely mounted on the body and the body turns within the grip during the operation. A single actuator rod which cams the blades from their open to their closed positions as well as retracting them, is keyed in a sturdy manner to the body so that the rotation of the actuator rod rotates the body and hence the blades within the handle grip as mentioned. A handle is removably attached to a proximal end of the actuator rod for facilitating combined rotation of the body and axial advance of the acutator rod for camming the blades during the operation.

In a modified form of the invention, rotation of the actuator handle automatically operates a screw mechanism, advancing the blades while they are rotating during the operation.

In addition to the features of presenting a smooth contour instrument without obstructions, the instrument of the present invention is constructed so that all of the instrument can be readily and completely disassembled for individual sterilization and possibly replacement of parts. The only tool required is a screw driver for removing four screws that hold the tip of the body portion to the main body portion for retaining the blade assembly. In the first embodiment of the invention, all the other parts are removed by simply flipping off two rubber O-rings and associated parts whereupon the various elements of the apparatus can be completely disassembled and sterilized individually, if required.

BRIEF DESCRIPTION OF THE DRAWINGS

FIG. 1 is a diagramatic view showing the distal end of the instrument during performance of an operation and indicating the specimen removed by the instrument.

FIG. 2 is a perspective view of the blade assembly.

FIG. 3 is a diagram showing the path of the blade during a portion of the helicoid cutting operation performed by the instrument.

FIG. 4 is a general view of the instrument, as seen when looking at the end of the pin that pivotally mounts the blades.

FIG. 5 is an enlarged, shortened section through the instrument, viewed as in FIG. 4, and showing the blades in their open or retracted position.

FIGS. 6 and 7 are sections taken as indicated on FIG. 5.

FIG. 8 is a veiw like FIG. 5 showing the blades in their advanced or closed position.

FIG. 9 is a still further enlarged view of the distal end of the instrument and seen as indicated at 9 — 9 on FIG. 4.

FIG. 10 is an enlarged view like that of FIG. 9 with parts broken away and viewed as the instrument appears in FIG. 5.

FIG. 11 is a section taken at 11 — 11 of FIG. 10.

FIG. 12 is a view of the body end portion and the blade assembly when removed from the main body portion and as viewed in the direction indicated at 12 — 12 on FIG. 10.

FIG. 13 is a section taken as indicated at 13 — 13 of FIG. 10.

FIG. 14 is a diagramatic perspective showing the blades partially disassembled but lined up to receive the pivot pin.

FIG. 15 is a view of the cam end of the actuator viewed as looking along line 15 — 15 of FIG. 11.

FIG. 16 is a central longitudinal section of a modified form wherein the blades are automatically closed as the actuator is rotated, the blades being open or retracted.

FIG. 17 is a section like that of FIG. 16, with blades closed or advanced.

PRINCIPLES OF BLADE OPERATION

FIG. 1 shows an instrument 10 of the present invention in place for performance of a conization operation on the uterene cervix C. The instrument 10 includes a two part body indicated generally at 12 and having an elongated main portion 13 and a separate distal end portion 14 secured to the main body portion by four screws 15, two of which appear in FIG. 1. The end portion 14 includes a top or obturator 16 for insertion into the endocervical canal, which tip is grooved at 17 to receive the blades when they are fully advanced to their closed condition. The end portion 14 of the body includes a flange 18 which serves as a stop and has rounded locater projections 18a (FIGS. 10 and 12). The stop flange 18 is secured to an enlarged flange 19 on the main body portion 13 by the aforesaid screws 15 and as mentioned, the flange 18 serves as a stop for controlling insertion of the instrument. Two round nosed, side cutting blades 20, 20a are pivotally mounted on a pin 21 (FIG. 2) having flat end portions 21a that are clamped between the two body portion flanges 18, 19 for retaining the blades in the instrument.

As will be described in detail presently, the blades 20, 20a are simultaneously rotated and are progressively advanced or closed by a combined rotary and linear motion of an actuator indicated generally at 30. In FIG. 1, it will be understood that only the distal end of the instrument appears. During the operation, as the blades are simultaneously rotated and advanced (closed) along arcuate paths, the blades follow a helicoid path partially and diagramatically indicated at "p" in FIG. 3, and the progressive side cutting action of the rotating blades 20, 20a, which are slowly advanced or closed during the operation readily removes a specimen such as that indicated at "a" in FIG. 1.

GENERAL APPEARANCE OF THE INSTRUMENT

FIG. 4 gives the overall appearance of the entire instrument of the present invention and reveals its smooth clean design with no rotary protuberances that project radially past the cutting blades 20, 20a. In addition to the parts just described in FIG. 1, FIG. 4 shows a handle 32 which is keyed to the proximal end of the blade actuator indicated generally at 30, and which is rotated while being simultaneously linearly advanced to close the blades during the operation. Also appearing in FIG. 4 is a grip 40 for the other hand of the surgeon. The grip 40 is a sleeve-like member in which the body 12 freely rotates during the operation and the grip is preferably provided with projections 41 to assist in steadying and guiding the instrument during the operation.

BLADE OR KNIFE CONSTRUCTION

The blades or knives 20, 20a have been briefly mentioned but an important feature of the present invention is the blade construction for cam operation, which obviates the need for linkages and externally protruding devices that rotate during the operation and hence present hazards. Also, the blades freely slip over the pivot pin 21, and the blade parts can be completely disassembled for sterilization, sharpening or replacement by removing the four screws 15 previously mentioned.

ADDITIONAL BLADE DETAILS

The general nature of the blades 20, 20a has been previously described with reference to FIG. 2. In addition to FIG. 2 reference is further made to Figures such as FIGS. 10 and 12 – 14 which show additional details of the blades. The blades 20, 20a are of basically the same construction, except that due to the manner in which they are hinged, they can be regarded as being of right and left hand with relation to their hinge construction. Referring to the blade 20 by way of example, it being understood that the blade 20a is of the same construction except for the offsetting of its hinge parts, the cutting portion of the blade is preferably formed so it will lie in a semi-spherical surface, and each blade has a rounded nose 22 best seen in FIGS. 9 and 14 and a curved cutting edge 23 which is sharpened in the direction of rotation of the body, this direction being to the right as viewed from the proximal end of the instrument.

Each of the blades projects from the end of an arm 24, the outer end of the arm also being machined to lie in a semi-spherical surface. A similar arm 24a is provided for the blade 20a. In order to permit pivotal mounting of the blades, the inner ends of the arms 24, 24a are provided with hinged sectors 25, 25a. These sectors are apertured in the usual manner to snugly receive the hinge pin 21 having flattened ends 21a as previously described.

As mentioned, the feature of the present invention is the non-projecting, substantially concealed operation of the blades. In order to provide for this compact mode of operation, each of the blade mounting arms 24, 24a has milled therein in a straight groove 26, 26a and each of these grooves is formed with semi-cylindrical sidewalls that provide cam surfaces. In order to receive the cam actuating mechanism associated with the actuator 30, previously mentioned in general, the cam grooves 26, 26a have rearwardly facing slots 27, 27a to receive an actuator cam device. As will be described presently, the opposed semi-cylindrical cam surfaces of the grooves 26, 26a each receive a simple hemi-spherical cam element integral with the actuator 30 previously mentioned.

ACTUATOR AND BODY ASSEMBLY

In accordance with the present invention, the blade actuator 30 is slidably mounted in the main portion 13 of the body 12 for advancing and retracting the blades 20, 20a. Also, the actuator 30 is keyed directly to the main body portion 13 so that rotation of the actuator handle 32 rotates the entire body 12 and the blades pivotally mounted therein. Referring to FIGS. 5 and 8, actuator 30 is a rod-like member having enlarged end portions 33, 34 which slidably fit into corresponding bores in the main body portion 13 and having a reduced intermediate portion 35 to minimize friction. In order to key the body to the actuator the distal end of the actuator 30 is formed with a key or vane 36, which is notched and silver soldered into opposed grooves formed in the end portion 33 of the actuator (FIG. 11). The vane 36 slides in a slot 39 formed near the end of the main body portion 13, as best seen in FIG. 9. This construction keys the body 12 to the actuator 30 so that rotation of the actuator handle 32 turns the body and hence the blades 20, 20a, without placing any strain on the blade mounting mechanism.

In order to advance and retract the blades, the actuator vane 36 is provided with a pair of cams 44, 44a (FIGS. 9 – 11) having hemispherical ends that slidably fit within the semi-cylindrical side walls of the blade arm grooves 26, 26a. The end of the actuator vane 36 is relieved at 48 (FIG. 10) to clear the blade hinge sectors 25, 25a when the actuator is advanced to close the blades. The main body portion 13 has an enlarged slot 50 (FIGS. 9 and 13) for receiving the blades 20, 20a and the end portion 14 of the body is provided with a slot or groove 52 that forms a continuation of the body slot 50 as seen in FIG. 9. With this construction, linear motion of the actuator 30 in the body 12 cams the blades between their open and closed positions (FIGS. 5 and 8) and yet none of the blade operating structure projects past the outer peripheries of the blades themselves.

ASSEMBLY OF THE HANDLE WITH THE ACTUATOR

Referring to FIGS. 5 and 6, the handle 32 is detachably assembled with the actuator 30 so that all parts are readily removed for sterilization. The handle 32 is bored at 60 (FIG. 5) to receive the enlarged end portion 34 of the actuator. The proximal end of the actuator is cross slotted at 61 and the handle is cross slotted at 62 (FIG. 5) to receive a key 64, the periphery of which is rounded to follow the contour of the associated portion of the handle (FIG. 6). The key 64 is detachably held in its driving position by a detachable sleeve 66 which sleeve is retained by a readily removable rubber O-ring 68 fitting into a semicylindrical groove formed in the handle 32. Thus, by removing the O-ring 68, the sleeve 66 and the key 64, the handle 32 can be removed, and all these parts are completely disassembled for sterilization.

ASSEMBLY OF THE GRIP AND BODY

After the actuator handle 32 has been removed, the grip 40 is also readily removed from the body. The grip 40 is retained on the body between a body shoulder 70 (FIG. 5) and the opposed ends of split ring sections 72, 73. These ring sections are internally grooved to snugly receive a low flange 74 formed on the body, which construction also fixes the axial position of the split ring sections 72, 73. The ring sections are held in their assembled position by a removable sleeve 76 and the sleeve, in turn, is retained on the ring sections by a removable O-ring 78, formed of neoprene or the like, which ring is a duplicate of the O-ring 68 that retains the actuator handle in place. Thus, after the handle 32 has been removed from the actuator in the manner just described, the grip 40 can be removed from the body by removing the O-ring 78, the sleeve 76 and the split ring sections 72, 73 whereupon the grip 40 can be slipped entirely free of the body and the actuator.

Complete disassembly of the instrument is accomplished by removing the screws 15, the body tip portion 14, the blades 20, 20a and the blade pivot pin 21, as previously described. Thus every part of the instrument can be fully exposed for sterilization.

USE OF THE INSTRUMENT

Although the use of the instrument of the present invention has been outlined briefly, it will be herein summarized. During the operation access to the cervix is provided in accordance with conventional surgical techniques, which need not be described in detail. The blades 20, 20a re retracted to the position of FIGS. 1 and 4 by holding the grip 40 with one hand and drawing the handle 32 toward the operator with the other hand. The tip of the obturator 16 is inserted into the endocervical canal, this motion being limited by the stop flange 18, behind the tip, (FIG. 1). The instrument is now manipulated by holding the grip 40 in one hand and rotating the handle 32 by the other hand, which action rotates the entire body 12 and hence the blades 20, 20a.

As the body and blades are thus rotated, the handle 32 is slowly advanced to close the blades. Since the ends or noses of the blades are rounded (FIG. 9) a certain amount of resistance to closing of the blades develops to provide a "feel" as to blade position. As a result, closing of the blades proceeds uniformly during rotation thereof to produce the helicoid cutting path "p" illustrated diagrammatically in FIG. 3.

Near the end of the cutting path the rounded noses of the blade rotatably enter the groove 17 (FIG. 9) in the tip 16 so that further rotation of the blades, even though they are brought up against the wall of the groove 18 in the tip and hence can close no further, produces a final rotary cut that severs the specimen "a" (FIG. 1). The instrument is now withdrawn from the site of the operation bringing the clean and smoothly cut specimen "a" with it. Because of the smoothly contoured, non-projecting nature of the instrument, this operation is performed without damage to surrounding tissue.

MODIFIED FORM

In the modification shown in FIGS. 16 and 17, the helicoid path "p" of FIG. 3 is obtained automatically, after insertion of the instrument, by simply rotating the handle 32a attached to the blade actuator rod 30a. In the description of the modified form of the invention, the reference characters for parts which are like those previously described are repeated, similar parts include a subscript letter and new reference numbers are applied only to parts that have no previous exact counterparts.

In the modified form of the invention, the major portion 13a of the body 12a is rotatable within and is axially fixed relative to the grip 40a, as in the previous embodiment. However, in this embodiment the handle 32a, connected to the actuator 30a for camming the blades closed, is externally threaded into threads formed internally in the grip 40a, so that rotation of the handle 32a not only rotates the body 12a and the blades 20, 20a as before, but by means of the aforesaid construction causes the actuator 30a to advance relative to the rotating body. This closes the blades as they rotate and automatically produce the helicoid cut previously described.

In the automatic form the handle 32a includes a major portion 80 that is keyed at 82 to the actuator rod 30a. The handle portion 80 and the actuator rod 30a are retained together by a cap nut 84. The handle portion 80 has a reduced diameter extension 85 which is externally threaded with Acme threads 86 for cooperation with mating threads 87 in the grip 40a. The grip 40a is rotatably mounted on the body portion 13a but is acially fixed relative to the body. The grip 40a has an internal bore 90 that is rotatable on the body portion 13a and the body portion has a radial flange 92 for axially locating the grip. The grip is rotatably clamped against the body flange 92 by means of a friction washer 94 and a clamp nut 96 threaded onto the grip. As mentioned, the grip has internal threads 87 that mate with the external threads 86 on the handle portion extension 85 and the grip is counterbored at 102 to receive the handle portion 80.

Before the operation the surgeon grasps the grip 40a with one hand and the handle 32a with the other and rotates the handle 32a in the direction which causes the body portion 80 to be pulled out along the grip. This pulls back on the actuator rod 30a and opens the blades as shown in FIG. 16. The required direction of rotation of the handle is determined by the hand of the threads 86, 87.

The instrument is then inserted in the manner previously described and the handle 32a is rotated in the opposite direction so that the cooperating threads 86, 87 on the handle and the grip cause the actuator rod 30a to advance and slowly cam the blades 20, 20a toward their closed position. While this takes place, because of the keyed connection 82 between the handle 32a and the actuator rod 30a, and because of the sliding key connection 36 between the distal end of the actuating rod and the body 12a previously described, the body rotates and the blades 20, 20a rotate with the body, as they are advanced or closed by the screw construction just described. As a result the tips of the cutter blade take the helicoid path "p" shown in FIG. 3 and a specimen "a" like that of FIG. 1 is excised. It is to be noted that the groove 17 in the tip 16 is deep enough so that the last partial revolution of the handle, as the blades complete their incision, permits the blade to be cammed towards a closed position and into the groove 17 so that the final segment of tissue is cut at the end of the manipulation of the instrument.

It is to be noted that as in the previous embodiment there are no objectionable obstructions or projections on the portions of the instrument received in the body cavity and that all portions of the instrument can be completely disassembled from one another for sterilization if desired.

Although the best mode contemplated for carrying out the present invention has been herein shown and described, it will be apparent that modification and variation may be made without departing from what is regarded to be the subject matter of the invention.

I claim:

1. An instrument for conization of the cervix of the type comprising an elogate body having a cervical body tip, a diametrical slot in said body behind said tip, opposed extendable and retractable knives pivotally mounted on said body within said slot, actuator means slidable within said body for advancing and retracting said knives, and a grip within which said body rotates; the improvement wherein said knives have radial mounting arms with radial cam follower means, said actuator means comprising a single rod keyed to and slidable along the axis of said body, a handle on the proximal end of said rod, and two cams on said actuator means disposed entirely within said body slot each cam making positive camming engagement with the cam follower means on one of said knife arms for pivoting said knives in both directions, said knives having rounded ends with side cutting edges for making continuous helical incisions as the body and knives are rotated and the knives are progressively advanced during said rotation by means of said rod.

2. The instrument of claim 1, wherein said cam follower means comprises a slot in each of said radial knife mounting arm.

3. The instrument of claim 2, wherein each of said cams projects laterally from a flat key member on the end of said actuator rod, said key member being slidably keyed to a diametral slot in said body.

4. The instrument of claim 1, wherein said tip projects from a stop flange, said knives being longitudinally curved with said pivot at the center of curvature, said knives closely overlying said stop flange.

5. The instrument of claim 1, comprising an external thread on said actuator means, said grip having a mating internal thread so that rotation of said actuator means handle while said grip is held both rotates said body and knives and pivots said knives.

6. An instrument for conization of the cervix of the type comprising a body having a cervical body tip, opposed extendable and retractable knife means pivoted on said body behind said tip, and actuator means comprising a single rod slidable within said body for advancing and retracting said knife means; the improvement comprising a hand grip within which said body rotates, a diametral slot formed in said body, a pair of knives pivoted to said body within said slot, means for slidably keying said rod to said body so that rotation of said rod rotates said body within said hand grip and hence rotates said knives, and means for connecting said single rod to both knives to advance and retract the knives when the rod is slid back and forth in said body, said knives having rounded ends with side cutting edges for making a helical incision as the body is rotated and as the knives are progressively advanced during said rotation by means of simultaneously rotating and advancing said rod.

7. An instrument for conization of the cervix of the type comprising an elongate body having a cervical body tip, a diametrical slot in said body behind said tip, an opposed extendable and retractable knife pivotally mounted on said body within said slot, actuator means slidable within said body for advancing and retracting said knife, and a grip within which said body rotates; the improvement wherein said knife has a radial mounting arm formed with cam follower means, said actuator means comprising a single rod keyed to and slidable along the axis of said body, a handle on the proximal end of said rod, and cam means on the distal end of said rod, said cam means making positive camming engagement with the cam follower means on said knife arm for pivoting said knife in both directions, said knife having a rounded end with a side cutting edge for making a continuous helical incision as the body and knife are rotated and the knife is progressively advanced during said rotation by means of said rod.

8. An instrument for conization of the cervix of the type comprising an elongate body having a cervical body tip, a diametrical slot in said body behind said tip, an extendable and a retractable knife pivotally mounted on said body within said slot, actuator means slidable within said body for advancing and retracting said knife, and a grip within which said slot, actuator means slidable within said body for advancing and retracting said knife, and a grip within which said body rotates; the improvement wherein said knife has a radial mounting arm with radial cam follower means, said actuator means comprising a single rod keyed to said body and slidable along the axis of said body, a handle on the proximal end of said rod, and cam means rigidly mounted on the distal end of said actuator means and disposed within said body slot, said cam means making positive camming engagement with the cam follower means on said knife arm for pivoting said knife in both directions, said cam means keying said rod to said body, said knife having a rounded end with a side cutting edge for making a continuous helical incision as the body and knife are rotated and the knife is progressively advanced during said rotation by axial motion of said rod.

9. An instrument for conization of the cervix of the type comprising a body having a cervical body tip, opposed extendable and retractable knife means pivoted on said body behind said tip, and actuator means comprising a single rod slidable within said body for advancing and retracting said knife means; the improvement comprising a hand grip within which said body rotates, said knife means comprising a pair of knives pivoted to said body within said slot, means for connecting said rod to said body so that rotation of said rod rotates said body within said hand grip and hence rotates said knives, and means for connecting said single rod to both knives to advance and retract the knives when the rod is slid back and forth in said body, said knives having rounded ends with side cutting edges for making a helical incision as the body is rotated and as the knives are progressively advanced during said rotation by means of simultaneously rotating and advancing said rod.

* * * * *